US008748144B2

(12) United States Patent
Kodama et al.

(10) Patent No.: US 8,748,144 B2
(45) Date of Patent: Jun. 10, 2014

(54) MUTANT FIREFLY LUCIFERASE, ITS GENE AND METHOD FOR PRODUCING MUTANT FIREFLY LUCIFERASE

(75) Inventors: Yukako Kodama, Noda (JP); Eriko Yoshihara, Noda (JP)

(73) Assignee: Kikkoman Corporation, Noda-Shi, Chiba (JP)

( * ) Notice: Subject to any disclaimer, the term of this patent is extended or adjusted under 35 U.S.C. 154(b) by 21 days.

(21) Appl. No.: 13/508,999

(22) PCT Filed: Feb. 16, 2010

(86) PCT No.: PCT/JP2010/052253
§ 371 (c)(1),
(2), (4) Date: May 15, 2012

(87) PCT Pub. No.: WO2011/058767
PCT Pub. Date: May 19, 2011

(65) Prior Publication Data
US 2012/0295325 A1    Nov. 22, 2012

(30) Foreign Application Priority Data

Nov. 10, 2009    (JP) .................................. 2009-256604
Dec. 22, 2009    (JP) ................................. 2009-289901

(51) Int. Cl.
*C12N 9/02* (2006.01)
*C12N 15/00* (2006.01)
*C07H 21/04* (2006.01)

(52) U.S. Cl.
USPC ....... 435/189; 536/23.1; 536/23.2; 435/320.1

(58) Field of Classification Search
None
See application file for complete search history.

(56) References Cited

U.S. PATENT DOCUMENTS 5,219,737 A  *   6/1993   Kajiyama et al. ............. 435/189
6,132,983 A       10/2000  Lowe et al.

FOREIGN PATENT DOCUMENTS

| JP | 9-510610 A | 8/1997 |
| JP | 2000-197487 A | 7/2000 |
| WO | WO 2007/017684 A2 | 2/2007 |

OTHER PUBLICATIONS

GenBank Accession No. ABZ88151, Jun. 2008, 2 pages.*
UniProt Database Accession No. B3TMS5, Feb. 2009, 1 page.*
Cho et al., Insect Mol. Biol. 8:193-200, 1999.*
Hattori N. et al., "Mutant luciferase enzymes from fireflies with increased resistance to benzalkonium chloride," *Biosci. Biotechnol. Biochem.*, 2002, vol. 66, No. 12, pp. 2587-2593.
Law Ghe et al., Mutagenesis of solvent-exposed amino acids in *Photinus pyralis* luciferase improves thermostability and pH-tolerance, *Biochem. J.*, 2006, vol. 397, No. 2, pp. 305-312.
Kajiyama N. et al., "Purification and characterization of luciferases from fireflies, *Luciola cruciata* and *Luciola lateralis*," *Biochim. Biophys. Acta.*, 1992, vol. 1120, No. 2, pp. 228-232.
Tatsumi H. et al., Molecular cloning and expression in *Escherichia coli* of a cDNA clone encoding luciferase of a firefly, *Luciola lateralis*, *Biochim. Biophys. Acta.*, 1992, vol. 1131, No. 2, pp. 161-165.
Yukako Kodama et al., "Luciferase Shinki Anteisei Kojo Hen'i no Shutoku," Koso Kogaku Kenkyukai Dai 62 Kai Koenkai Koen Yoshishu, Nov. 13, 2009, p. 74(C-1).
Bruce R. Branchini et al., "A Mutagenesis Study of the Putative Luciferin Binding Site Residues of Firefly Luciferase," *Biochemistry*, 2003, vol. 42, pp. 10429-10436.
English-language International Preliminary Report on Patentability and Written Opinion of the International Searching Authority dated Jun. 21, 2012 for International Application PCT/JP2010/052253 filed Feb. 16, 2010; Applicants: Kikkoman Corporation et al.
Supplementary European Search Report mailed Mar. 26, 2013 for EP 10829727.
Kajiyama N. et al., "Isolation and Characterization of Mutants of Firefly Luciferase Which Produce Different Colors of Light", *Protein Engineering*, vol. 4, No. 6, Aug. 4, 1991, pp. 691-694.
Etchebest C. et al., "A reduced amino acid alphabet for understanding and designing protein adaptation to mutation", *European Biophysics Journal; With Biophysics Letters*, Springer, Berlin, Germany, vol. 36, No. 8, Jun. 13, 2007.
Eiichi Nakano, "Hotaru Luciferase no Shinka," ("Evolution of a Firefly Luciferase"), *Biotechnology*, 1999, vol. 77, No. 10, pp. 426-428, along with an English-language translation thereof.
Japanese Office Action (Notification of Reasons for Rejection) (including an English-language translation thereof) dispatched on Jan. 15, 2014 for Japanese application 2009-289901.

* cited by examiner

*Primary Examiner* — David J Steadman
(74) *Attorney, Agent, or Firm* — Holtz Holtz Goodman & Chick PC

(57)    ABSTRACT

A Heike firefly luciferase having excellent thermostability and storage stability and a process for its production, wherein the amino acid corresponding to position 287 of Heike firefly luciferase is alanine.

4 Claims, 2 Drawing Sheets

```
SEQUENCE LISTING

<160> NUMBER OF SEQ ID NOS: 31

<210> SEQ ID NO 1
<211> LENGTH: 30
<212> TYPE: DNA
<213> ORGANISM: Artificial
<220> FEATURE:
<223> OTHER INFORMATION: primer 1

<400> SEQUENCE: 1
ggaattccat atggaaaaca tggagaacga                                      30

<210> SEQ ID NO 2
<211> LENGTH: 28
<212> TYPE: DNA
<213> ORGANISM: Artificial
<220> FEATURE:
<223> OTHER INFORMATION: primer 2

<400> SEQUENCE: 2
gtcaaggcta tggtgcaaca gaaacaac                                        28

<210> SEQ ID NO 3
<211> LENGTH: 28
```

```
<212> TYPE: DNA
<213> ORGANISM: Artificial
<220> FEATURE:
<223> OTHER INFORMATION: primer 3

<400> SEQUENCE: 3
gttgtttctg ttgcaccata gccttgac                                          28

<210> SEQ ID NO 4
<211> LENGTH: 1908
<212> TYPE: DNA
<213> ORGANISM: Luciola lateralis

<400> SEQUENCE: 4
atggaaaaca tggagaacga tgaaaatatt gtgtatggtc ctgaaccatt ttaccctatt         60
gaagagggat ctgctggagc acaattgcgc aagtatatgg atcgatatgc aaaacttgga        120
gcaattgctt ttactaacgc acttaccggt gtcgattata cgtacgccga atacttagaa        180
aaatcatgct gtctaggaga ggcttttaaag aattatggtt tggttgttga tggaagaatt       240
gcgttatgca gtgaaaactg tgaagagttc tttattcctg tattagccgg tttatttata       300
ggtgtcggtg tggctccaac taatgagatt tacactctac gtgaattggt tcacagttta       360
ggcatctcta agccaacaat tgtatttagt tctaaaaaag gattagataa agttataact       420
gtacaaaaaa cggtaactgc tattaaaacc attgttatat tggacagcaa agtggattat       480
agaggttatc aatccatgga caactttatt aaaaaaaaca ctccacaagg tttcaaagga       540
tcaagtttta aaactgtaga agttaaccgc aagaacaag ttgctcttat aatgaactct        600
tcgggttcaa ccggtttgcc aaaaggtgtg caacttactc atgaaaattt ggtcacgcgt       660
ttttctcacg ctagagatcc aatttatgga accaagtttt caccaggcac ggctatttta       720
actgtagtac cattccatca tggttttggt atgtttacta ctttaggcta tctaacttgt       780
ggttttcgta ttgtcatgtt aacgaaattt gacgaagaga ctttttttaaa aacactgcaa      840 gattacaaat gttcaagcgt tattcttgta ccgactttgt ttgcaattct aatagaagt        900 gaattactcg ataaatatga tttatcaaat ttagttgaaa ttgcatctgg cggagcacct       960
ttatctaaag aaattggtga agctgttgct agacgtttta atttaccggg tgttcgtcaa      1020
ggctatggtg caacagaaac aacctctgca attattatca caccggaagg cgatgataaa      1080
ccaggtgctt ctggcaaagt tgtgccatta tttaaagcaa aagttatcga tcttgatact      1140
aaaaaaactt tgggcccgaa cagacgtgga gaagtttgtg taagggtcc tatgcttatg       1200 aaaggttatg tagataatcc agaagcaaca agagaaatca tagatgaaga aggttggttg      1260
cacacaggag atattgggta ttacgatgaa gaaaaacatt tctttatcgt ggatcgtttg      1320
aagtctttaa tcaaatacaa aggatatcaa gtaccacctg ctgaattaga atctgttctt      1380
ttgcaacatc caaatatttt tgatgccggc gttgctggcg ttccagatcc tatagctggt      1440
gagcttccgg gagctgttgt tgtacttgaa aaggaaaat ctatgactga aaagaagta        1500 atggattacg ttgctagtca agtttcaaat gcaaaacgtt tgcgtggtgg tgtccgtttt      1560
gtggacgaag tacctaaagg tctcactggt aaaattgacg gtaaagcaat tagagaaata      1620
ctgaagaaac cagttgctaa gggatccatg gaagcgccag cagcagcgga atcagtggt       1680 cacatcgtac gttccccgat ggttggtact ttctaccgca ccccaagccc ggacgcaaaa     1740
gcgttcatcg aagtgggtca gaaagtcaac gtgggcgata ccctgtgcat cgttgaagcc      1800
atgaaaatga tgaaccagat cgaagcggac aaatccggta ccgtgaaagc aattctggtc      1860
gaaagtggac aaccggtaga atttgacgag ccgctggtcg tcatcgag                  1908
```

<210> SEQ ID NO 5
<211> LENGTH: 21
<212> TYPE: DNA
<213> ORGANISM: Artificial
<220> FEATURE:
<223> OTHER INFORMATION: primer 4

<400> SEQUENCE: 5
gcggccatat cgaaggtcgt c                                              21

<210> SEQ ID NO 6
<211> LENGTH: 30
<212> TYPE: DNA
<213> ORGANISM: Artificial
<220> FEATURE:
<223> OTHER INFORMATION: primer 5

<400> SEQUENCE: 6
ctcatgtttg acagcttatc atcgataagc                                     30

<210> SEQ ID NO 7
<211> LENGTH: 636
<212> TYPE: PRT
<213> ORGANISM: Luciola lateralis

<400> SEQUENCE: 7

Met Glu Asn Met Glu Asn Asp Glu Asn Ile Val Tyr Gly Pro Glu Pro
1               5                   10                  15

Phe Tyr Pro Ile Glu Glu Gly Ser Ala Gly Ala Gln Leu Arg Lys Tyr
            20                  25                  30

Met Asp Arg Tyr Ala Lys Leu Gly Ala Ile Ala Phe Thr Asn Ala Leu
        35                  40                  45

Thr Gly Val Asp Tyr Thr Tyr Ala Glu Tyr Leu Glu Lys Ser Cys Cys
    50                  55                  60

Leu Gly Glu Ala Leu Lys Asn Tyr Gly Leu Val Val Asp Gly Arg Ile
65                  70                  75                  80

Ala Leu Cys Ser Glu Asn Cys Glu Glu Phe Phe Ile Pro Val Leu Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Ala Ile Lys Thr Ile Val Ile Leu Asp Ser Lys Val Asp Tyr
145                 150                 155                 160

Arg Gly Tyr Gln Ser Met Asp Asn Phe Ile Lys Lys Asn Thr Pro Gln
                165                 170                 175

Gly Phe Lys Gly Ser Ser Phe Lys Thr Val Glu Val Asn Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Leu Val Thr Arg Phe Ser His Ala
    210                 215                 220

Arg Asp Pro Ile Tyr Gly Asn Gln Val Ser Pro Gly Thr Ala Ile Leu
225                 230                 235                 240

Thr Val Val Pro Phe His His Gly Phe Gly Met Phe Thr Thr Leu Gly
                245                 250                 255

Tyr Leu Thr Cys Gly Phe Arg Ile Val Met Leu Thr Lys Phe Asp Glu
            260                 265                 270

Glu Thr Phe Leu Lys Thr Leu Gln Asp Tyr Lys Cys Ser Ser Ala Ile
        275                 280                 285

Leu Val Pro Thr Leu Phe Ala Ile Leu Asn Arg Ser Glu Leu Leu Asp
290                 295                 300

Lys Tyr Asp Leu Ser Asn Leu Val Glu Ile Ala Ser Gly Gly Ala Pro
305                 310                 315                 320

Leu Ser Lys Glu Ile Gly Glu Ala Val Ala Arg Arg Phe Asn Leu Pro
                325                 330                 335

Gly Val Arg Gln Gly Tyr Gly Ala Thr Glu Thr Thr Ser Ala Ile Ile
            340                 345                 350

Ile Thr Pro Glu Gly Asp Asp Lys Pro Gly Ala Ser Gly Lys Val Val
        355                 360                 365

Pro Leu Phe Lys Ala Lys Val Ile Asp Leu Asp Thr Lys Lys Thr Leu
370                 375                 380

Gly Pro Asn Arg Arg Gly Glu Val Cys Val Lys Gly Pro Met Leu Met
385                 390                 395                 400

Lys Gly Tyr Val Asp Asn Pro Glu Ala Thr Arg Glu Ile Ile Asp Glu
                405                 410                 415

Glu Gly Trp Leu His Thr Gly Asp Ile Gly Tyr Tyr Asp Glu Glu Lys
            420                 425                 430

His Phe Phe Ile Val Asp Arg Leu Lys Ser Leu Ile Lys Tyr Lys Gly
        435                 440                 445

Tyr Gln Val Pro Pro Ala Glu Leu Glu Ser Val Leu Leu Gln His Pro
450                 455                 460

Asn Ile Phe Asp Ala Gly Val Ala Gly Val Pro Asp Pro Ile Ala Gly
465                 470                 475                 480

Glu Leu Pro Gly Ala Val Val Val Leu Glu Lys Gly Lys Ser Met Thr
                485                 490                 495

Glu Lys Glu Val Met Asp Tyr Val Ala Ser Gln Val Ser Asn Ala Lys
            500                 505                 510

Arg Leu Arg Gly Gly Val Arg Phe Val Asp Glu Val Pro Lys Gly Leu
        515                 520                 525

Thr Gly Lys Ile Asp Gly Lys Ala Ile Arg Glu Ile Leu Lys Lys Pro
530                 535                 540

Val Ala Lys Gly Ser Met Glu Ala Pro Ala Ala Ala Glu Ile Ser Gly
545                 550                 555                 560

His Ile Val Arg Ser Pro Met Val Gly Thr Phe Tyr Arg Thr Pro Ser
                565                 570                 575

Pro Asp Ala Lys Ala Phe Ile Glu Val Gly Gln Lys Val Asn Val Gly
            580                 585                 590

Asp Thr Leu Cys Ile Val Glu Ala Met Lys Met Met Asn Gln Ile Glu
        595                 600                 605

Ala Asp Lys Ser Gly Thr Val Lys Ala Ile Leu Val Glu Ser Gly Gln
610                 615                 620

Pro Val Glu Phe Asp Glu Pro Leu Val Val Ile Glu
625                 630                 635

<210> SEQ ID NO 8
<211> LENGTH: 636
<212> TYPE: PRT
<213> ORGANISM: Luciola lateralis

<400> SEQUENCE: 8

```
Met Glu Asn Met Glu Asn Asp Glu Asn Ile Val Tyr Gly Pro Glu Pro
1               5                   10                  15
Phe Tyr Pro Ile Glu Glu Gly Ser Ala Gly Ala Gln Leu Arg Lys Tyr
                20                  25                  30
Met Asp Arg Tyr Ala Lys Leu Gly Ala Ile Ala Phe Thr Asn Ala Leu
            35                  40                  45
Thr Gly Val Asp Tyr Thr Tyr Ala Glu Tyr Leu Glu Lys Ser Cys Cys
        50                  55                  60
Leu Gly Glu Ala Leu Lys Asn Tyr Gly Leu Val Val Asp Gly Arg Ile
65                  70                  75                  80
Ala Leu Cys Ser Glu Asn Cys Glu Glu Phe Ile Pro Val Leu Ala
                85                  90                  95
Gly Leu Phe Ile Gly Val Gly Val Ala Pro Thr Asn Glu Ile Tyr Thr
                100                 105                 110
Leu Arg Glu Leu Val His Ser Leu Gly Ile Ser Lys Pro Thr Ile Val
            115                 120                 125
Phe Ser Ser Lys Lys Gly Leu Asp Lys Val Ile Thr Val Gln Lys Thr
            130                 135                 140
Val Thr Ala Ile Lys Thr Ile Val Ile Leu Asp Ser Lys Val Asp Tyr
145                 150                 155                 160
Arg Gly Tyr Gln Ser Met Asp Asn Phe Ile Lys Lys Asn Thr Pro Gln
                165                 170                 175
Gly Phe Lys Gly Ser Ser Phe Lys Thr Val Glu Val Asn Arg Lys Glu
            180                 185                 190
Gln Val Ala Leu Ile Met Asn Ser Ser Gly Ser Thr Gly Leu Pro Lys
            195                 200                 205
Gly Val Gln Leu Thr His Glu Asn Leu Val Thr Arg Phe Ser His Ala
            210                 215                 220
Arg Asp Pro Ile Tyr Gly Asn Gln Val Ser Pro Gly Thr Ala Ile Leu
225                 230                 235                 240
Thr Val Val Pro Phe His His Gly Phe Gly Met Phe Thr Thr Leu Gly
                245                 250                 255
Tyr Leu Thr Cys Gly Phe Arg Ile Val Met Leu Thr Lys Phe Asp Glu
            260                 265                 270
Glu Thr Phe Leu Lys Thr Leu Gln Asp Tyr Lys Cys Ser Ser Val Ile
            275                 280                 285
Leu Val Pro Thr Leu Phe Ala Ile Leu Asn Arg Ser Glu Leu Leu Asp
            290                 295                 300
Lys Tyr Asp Leu Ser Asn Leu Val Glu Ile Ala Ser Gly Gly Ala Pro
305                 310                 315                 320
Leu Ser Lys Glu Ile Ser Glu Ala Val Ala Arg Phe Asn Leu Pro
                325                 330                 335
Gly Val Arg Gln Gly Tyr Gly Leu Thr Glu Thr Thr Ser Ala Ile Ile
            340                 345                 350
Ile Thr Pro Glu Gly Asp Asp Lys Pro Gly Ala Ser Gly Lys Val Val
            355                 360                 365
Pro Leu Phe Lys Ala Lys Val Ile Asp Leu Asp Thr Lys Lys Thr Leu
            370                 375                 380
Gly Pro Asn Arg Arg Gly Glu Val Cys Val Lys Gly Pro Met Leu Met
385                 390                 395                 400
Lys Gly Tyr Val Asp Asn Pro Glu Ala Thr Arg Glu Ile Ile Asp Glu
                405                 410                 415
Glu Gly Trp Leu His Thr Gly Asp Ile Gly Tyr Tyr Asp Glu Glu Lys
```

```
                    420                 425                 430
His Phe Phe Ile Val Asp Arg Leu Lys Ser Leu Ile Lys Tyr Lys Gly
            435                 440                 445

Tyr Gln Val Pro Pro Ala Glu Leu Glu Ser Val Leu Leu Gln His Pro
    450                 455                 460

Asn Ile Phe Asp Ala Gly Val Ala Gly Val Pro Asp Pro Ile Ala Gly
465                 470                 475                 480

Glu Leu Pro Gly Ala Val Val Leu Glu Lys Gly Lys Ser Met Thr
                485                 490                 495

Glu Lys Glu Val Met Asp Tyr Val Ala Ser Gln Val Ser Asn Ala Lys
            500                 505                 510

Arg Leu Arg Gly Gly Val Arg Phe Val Asp Glu Val Pro Lys Gly Leu
        515                 520                 525

Thr Gly Lys Ile Asp Gly Lys Ala Ile Arg Glu Ile Leu Lys Lys Pro
    530                 535                 540

Val Ala Lys Gly Ser Met Glu Ala Pro Ala Ala Ala Glu Ile Ser Gly
545                 550                 555                 560

His Ile Val Arg Ser Pro Met Val Gly Thr Phe Tyr Arg Thr Pro Ser
                565                 570                 575

Pro Asp Ala Lys Ala Phe Ile Glu Val Gly Gln Lys Val Asn Val Gly
            580                 585                 590

Asp Thr Leu Cys Ile Val Glu Ala Met Lys Met Met Asn Gln Ile Glu
        595                 600                 605

Ala Asp Lys Ser Gly Thr Val Lys Ala Ile Leu Val Glu Ser Gly Gln
    610                 615                 620

Pro Val Glu Phe Asp Glu Pro Leu Val Val Ile Glu
625                 630                 635

<210> SEQ ID NO 9
<211> LENGTH: 636
<212> TYPE: PRT
<213> ORGANISM: Luciola lateralis

<400> SEQUENCE: 9

Met Glu Asn Met Glu Asn Asp Glu Asn Ile Val Tyr Gly Pro Glu Pro
1               5                   10                  15

Phe Tyr Pro Ile Glu Glu Gly Ser Ala Gly Ala Gln Leu Arg Lys Tyr
            20                  25                  30

Met Asp Arg Tyr Ala Lys Leu Gly Ala Ile Ala Phe Thr Asn Ala Leu
        35                  40                  45

Thr Gly Val Asp Tyr Thr Tyr Ala Glu Tyr Leu Glu Lys Ser Cys Cys
    50                  55                  60

Leu Gly Glu Ala Leu Lys Asn Tyr Gly Leu Val Val Asp Gly Arg Ile
65                  70                  75                  80

Ala Leu Cys Ser Glu Asn Cys Glu Glu Phe Phe Ile Pro Val Leu Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Ala Ile Lys Thr Ile Val Ile Leu Asp Ser Lys Val Asp Tyr
145                 150                 155                 160

Arg Gly Tyr Gln Ser Met Asp Asn Phe Ile Lys Lys Asn Thr Pro Gln
```

-continued

```
                165                 170                 175
Gly Phe Lys Gly Ser Ser Phe Lys Thr Val Glu Val Asn Arg Lys Glu
            180                 185                 190
Gln Val Ala Leu Ile Met Asn Ser Ser Gly Ser Thr Gly Leu Pro Lys
        195                 200                 205
Gly Val Gln Leu Thr His Glu Asn Leu Val Thr Arg Phe Ser His Ala
    210                 215                 220
Arg Asp Pro Ile Tyr Gly Asn Gln Val Ser Pro Gly Thr Ala Ile Leu
225                 230                 235                 240
Thr Val Val Pro Phe His His Gly Phe Gly Met Phe Thr Thr Leu Gly
                245                 250                 255
Tyr Leu Thr Cys Gly Phe Arg Ile Val Met Leu Thr Lys Phe Asp Glu
            260                 265                 270
Glu Thr Phe Leu Lys Thr Leu Gln Asp Tyr Lys Cys Ser Ser Val Ile
        275                 280                 285
Leu Val Pro Thr Leu Phe Ala Ile Leu Asn Arg Ser Glu Leu Leu Asp
    290                 295                 300
Lys Tyr Asp Leu Ser Asn Leu Val Glu Ile Ala Ser Gly Gly Ala Pro
305                 310                 315                 320
Leu Ser Lys Glu Ile Gly Glu Ala Val Ala Arg Arg Phe Asn Leu Pro
                325                 330                 335
Gly Val Arg Gln Gly Tyr Gly Ala Thr Glu Thr Thr Ser Ala Ile Ile
            340                 345                 350
Ile Thr Pro Glu Gly Asp Asp Lys Pro Gly Ala Ser Gly Lys Val Val
        355                 360                 365
Pro Leu Phe Lys Ala Lys Val Ile Asp Leu Asp Thr Lys Lys Thr Leu
    370                 375                 380
Gly Pro Asn Arg Arg Gly Glu Ile Cys Val Lys Gly Pro Met Leu Met
385                 390                 395                 400
Lys Gly Tyr Val Asp Asn Pro Glu Ala Thr Arg Glu Ile Ile Asp Glu
                405                 410                 415
Glu Gly Trp Leu His Thr Gly Asp Ile Gly Tyr Tyr Asp Glu Glu Lys
            420                 425                 430
His Phe Phe Ile Val Asp Arg Leu Lys Ser Leu Ile Lys Tyr Lys Gly
        435                 440                 445
Tyr Gln Val Pro Pro Ala Glu Leu Glu Ser Val Leu Leu Gln His Pro
    450                 455                 460
Asn Ile Phe Asp Ala Gly Val Ala Gly Val Pro Asp Pro Ile Ala Gly
465                 470                 475                 480
Glu Leu Pro Gly Ala Val Val Val Leu Glu Lys Gly Lys Ser Met Thr
                485                 490                 495
Glu Lys Glu Val Met Asp Tyr Val Ala Ser Gln Val Ser Asn Ala Lys
            500                 505                 510
Arg Leu Arg Gly Gly Val Arg Phe Val Asp Glu Val Pro Lys Gly Leu
        515                 520                 525
Thr Gly Lys Ile Asp Gly Lys Ala Ile Arg Glu Ile Leu Lys Lys Pro
    530                 535                 540
Val Ala Lys Gly Ser Met Glu Ala Pro Ala Ala Ala Glu Ile Ser Gly
545                 550                 555                 560
His Ile Val Arg Ser Pro Met Val Gly Thr Phe Tyr Arg Thr Pro Ser
                565                 570                 575
Pro Asp Ala Lys Ala Phe Ile Glu Val Gly Gln Lys Val Asn Val Gly
            580                 585                 590
```

```
Asp Thr Leu Cys Ile Val Glu Ala Met Lys Met Met Asn Gln Ile Glu
        595                 600                 605
Ala Asp Lys Ser Gly Thr Val Lys Ala Ile Leu Val Glu Ser Gly Gln
610                 615                 620
Pro Val Glu Phe Asp Glu Pro Leu Val Val Ile Glu
625                 630                 635

<210> SEQ ID NO 10
<211> LENGTH: 636
<212> TYPE: PRT
<213> ORGANISM: Luciola lateralis

<400> SEQUENCE: 10

Met Glu Asn Met Glu Asn Asp Glu Asn Ile Val Tyr Gly Pro Glu Pro
1               5                   10                  15
Phe Tyr Pro Ile Glu Glu Gly Ser Ala Gly Ala Gln Leu Arg Lys Tyr
                20                  25                  30
Met Asp Arg Tyr Ala Lys Leu Gly Ala Ile Ala Phe Thr Asn Ala Leu
            35                  40                  45
Thr Gly Val Asp Tyr Thr Tyr Ala Glu Tyr Leu Glu Lys Ser Cys Cys
    50                  55                  60
Leu Gly Glu Ala Leu Lys Asn Tyr Gly Leu Val Val Asp Gly Arg Ile
65                  70                  75                  80
Ala Leu Cys Ser Glu Asn Cys Glu Glu Phe Phe Ile Pro Val Leu Ala
                85                  90                  95
Gly Leu Phe Ile Gly Val Gly Val Ala Pro Thr Asn Glu Ile Tyr Thr
            100                 105                 110
Leu Arg Glu Leu Val His Ser Leu Gly Ile Ser Lys Pro Thr Ile Val
        115                 120                 125
Phe Ser Ser Lys Lys Gly Leu Asp Lys Val Ile Thr Val Gln Lys Thr
    130                 135                 140
Val Thr Ala Ile Lys Thr Ile Val Ile Leu Asp Ser Lys Val Asp Tyr
145                 150                 155                 160
Arg Gly Tyr Gln Ser Met Asp Asn Phe Ile Lys Lys Asn Thr Pro Gln
                165                 170                 175
Gly Phe Lys Gly Ser Ser Phe Lys Thr Val Glu Val Asn Arg Lys Glu
            180                 185                 190
Gln Val Ala Leu Ile Met Asn Ser Ser Gly Ser Thr Gly Leu Pro Lys
        195                 200                 205
Gly Val Gln Leu Thr His Glu Asn Leu Val Thr Arg Phe Ser His Ala
    210                 215                 220
Arg Asp Pro Ile Tyr Gly Asn Gln Val Ser Pro Gly Thr Ala Ile Leu
225                 230                 235                 240
Thr Val Val Pro Phe His His Gly Phe Gly Met Phe Thr Thr Leu Gly
                245                 250                 255
Tyr Leu Thr Cys Gly Phe Arg Ile Val Met Leu Thr Lys Phe Asp Glu
            260                 265                 270
Glu Thr Phe Leu Lys Thr Leu Gln Asp Tyr Lys Cys Ser Ser Val Ile
        275                 280                 285
Leu Val Pro Thr Leu Phe Ala Ile Leu Asn Arg Ser Glu Leu Leu Asp
    290                 295                 300
Lys Tyr Asp Leu Ser Asn Leu Val Glu Ile Ala Ser Gly Gly Ala Pro
305                 310                 315                 320
Leu Ser Lys Glu Ile Gly Glu Ala Val Ala Arg Arg Phe Asn Leu Pro
                325                 330                 335
```

Gly Val Arg Gln Gly Tyr Gly Ala Thr Glu Thr Ser Ala Ile Ile
            340                 345                 350

Ile Thr Pro Glu Gly Asp Asp Lys Pro Gly Ala Ser Gly Lys Val Val
        355                 360                 365

Pro Leu Phe Lys Ala Lys Val Ile Asp Leu Asp Thr Lys Lys Thr Leu
    370                 375                 380

Gly Pro Asn Arg Arg Gly Glu Val Cys Val Lys Gly Pro Met Leu Met
385                 390                 395                 400

Lys Gly Tyr Val Asp Asn Pro Glu Ala Thr Arg Glu Ile Ile Asp Glu
            405                 410                 415

Glu Gly Trp Leu His Thr Gly Asp Ile Gly Tyr Tyr Asp Glu Glu Lys
        420                 425                 430

His Phe Phe Ile Val Asp Arg Leu Lys Ser Leu Ile Lys Tyr Lys Gly
    435                 440                 445

Tyr Gln Val Pro Pro Ala Glu Leu Glu Ser Val Leu Leu Gln His Pro
450                 455                 460

Asn Ile Ile Asp Ala Gly Val Ala Gly Val Pro Asp Pro Ile Ala Gly
465                 470                 475                 480

Glu Leu Pro Gly Ala Val Val Val Leu Glu Lys Gly Lys Ser Met Thr
            485                 490                 495

Glu Lys Glu Val Met Asp Tyr Val Ala Ser Gln Val Ser Asn Ala Lys
        500                 505                 510

Arg Leu Arg Gly Gly Val Arg Phe Val Asp Glu Val Pro Lys Gly Leu
    515                 520                 525

Thr Gly Lys Ile Asp Gly Lys Ala Ile Arg Glu Ile Leu Lys Lys Pro
530                 535                 540

Val Ala Lys Gly Ser Met Glu Ala Pro Ala Ala Glu Ile Ser Gly
545                 550                 555                 560

His Ile Val Arg Ser Pro Met Val Gly Thr Phe Tyr Arg Thr Pro Ser
            565                 570                 575

Pro Asp Ala Lys Ala Phe Ile Glu Val Gly Gln Lys Val Asn Val Gly
        580                 585                 590

Asp Thr Leu Cys Ile Val Glu Ala Met Lys Met Met Asn Gln Ile Glu
    595                 600                 605

Ala Asp Lys Ser Gly Thr Val Lys Ala Ile Leu Val Glu Ser Gly Gln
610                 615                 620

Pro Val Glu Phe Asp Glu Pro Leu Val Val Ile Glu
625                 630                 635

<210> SEQ ID NO 11
<211> LENGTH: 1908
<212> TYPE: DNA
<213> ORGANISM: Luciola lateralis

<400> SEQUENCE: 11
atggaaaaca tggagaacga tgaaaatatt gtgtatggtc ctgaaccatt ttaccctatt      60
gaagagggat ctgctggagc acaattgcgc aagtatatgg atcgatatgc aaaacttgga     120
gcaattgctt tactaacgc acttaccggt gtcgattata cgtacgccga atacttagaa     180
aaatcatgct gtctaggaga ggctttaaag aattatggtt tggttgttga tggaagaatt     240
gcgttatgca gtgaaaactg tgaagagttc tttattcctg tattagccgg ttatttata      300 ggtgtcggtg tggctccaac taatgagatt tacactctac gtgaattggt tcacagttta     360
ggcatctcta agccaacaat tgtatttagt tctaaaaaag gattagataa agttataact     420
gtacaaaaaa cggtaactgc tattaaaacc attgttatat tggacagcaa agtggattat     480

```
agaggttatc aatccatgga caactttatt aaaaaaaaca ctccacaagg tttcaaagga    540
tcaagtttta aaactgtaga agttaaccgc aaagaacaag ttgctcttat aatgaactct    600 tcggttcaa ccggtttgcc aaaaggtgtg caacttactc atgaaaattt ggtcacgcgt    660
ttttctcacg ctagagatcc aatttatgga aaccaagttt caccaggcac ggctatttta    720
actgtagtac cattccatca tggttttggt atgtttacta ctttaggcta tctaacttgt    780
ggttttcgta ttgtcatgtt aacgaaattt gacgaagaga cttttttaaa aacactgcaa    840
gattacaaat gttcaagcgc tattctggta ccgactttgt ttgcaattct aatagaagt    900 gaattactcg ataaatatga tttatcaaat ttagttgaaa ttgcatctgg cggagcacct    960
ttatctaaag aaattggtga agctgttgct agacgtttta atttaccggg tgttcgtcaa   1020
ggctatggtg caacagaaac aacctctgca attattatca caccggaagg cgatgataaa   1080
ccaggtgctt ctggcaaagt tgtgccatta tttaaagcaa aagttatcga tcttgatact   1140
aaaaaaactt tgggcccgaa cagacgtgga gaagtttgtg taaagggtcc tatgcttatg   1200
aaaggttatg tagataatcc agaagcaaca agagaaatca tagatgaaga aggttggttg   1260
cacacaggag atattgggta ttacgatgaa gaaaaacatt tctttatcgt ggatcgtttg   1320
aagtctttaa tcaaatacaa aggatatcaa gtaccacctg ctgaattaga atctgttctt   1380
ttgcaacatc caaatatttt tgatgccggc gttgctggcg ttccagatcc tatagctggt   1440
gagcttccgg gagctgttgt tgtacttgaa aaggaaaat ctatgactga aaagaagta    1500 atggattacg ttgctagtca agtttcaaat gcaaacgtt tgcgtggtgg tgtccgtttt   1560
gtggacgaag tacctaaagg tctcactggt aaaattgacg gtaaagcaat tagagaaata   1620
ctgaagaaac cagttgctaa gggatccatg gaagcgccag cagcagcgga aatcagtggt   1680
cacatcgtac gttccccgat ggttggtact ttctaccgca ccccaagccc ggacgcaaaa   1740
gcgttcatcg aagtgggtca gaaagtcaac gtgggcgata ccctgtgcat cgttgaagcc   1800
atgaaaatga tgaaccagat cgaagcggac aaatccggta ccgtgaaagc aattctggtc   1860
gaaagtggac aaccggtaga atttgacgag ccgctggtcg tcatcgag              1908
```

```
<210> SEQ ID NO 12
<211> LENGTH: 28
<212> TYPE: DNA
<213> ORGANISM: Artificial
<220> FEATURE:
<223> OTHER INFORMATION: primer F

<400> SEQUENCE: 12
attctggtac cgactttgtt tgcaattc                                        28

<210> SEQ ID NO 13
<211> LENGTH: 27
<212> TYPE: DNA
<213> ORGANISM: Artificial
<220> FEATURE:
<223> OTHER INFORMATION: V287C-R

<400> SEQUENCE: 13
acagcttgaa catttgtaat cttgcag                                         27

<210> SEQ ID NO 14
<211> LENGTH: 27
<212> TYPE: DNA
<213> ORGANISM: Artificial
<220> FEATURE:
<223> OTHER INFORMATION: V287D-R
```

```
<400> SEQUENCE: 14
atcgcttgaa catttgtaat cttgcag                                              27

<210> SEQ ID NO 15
<211> LENGTH: 27
<212> TYPE: DNA
<213> ORGANISM: Artificial
<220> FEATURE:
<223> OTHER INFORMATION: V287E-R

<400> SEQUENCE: 15
ctcgcttgaa catttgtaat cttgcag                                              27

<210> SEQ ID NO 16
<211> LENGTH: 27
<212> TYPE: DNA
<213> ORGANISM: Artificial
<220> FEATURE:
<223> OTHER INFORMATION: V287F-R

<400> SEQUENCE: 16
aaagcttgaa catttgtaat cttgcag                                              27

<210> SEQ ID NO 17
<211> LENGTH: 27
<212> TYPE: DNA
<213> ORGANISM: Artificial
<220> FEATURE:
<223> OTHER INFORMATION: V287G-R

<400> SEQUENCE: 17
accgcttgaa catttgtaat cttgcag                                              27

<210> SEQ ID NO 18
<211> LENGTH: 27
<212> TYPE: DNA
<213> ORGANISM: Artificial
<220> FEATURE:
<223> OTHER INFORMATION: V287H-R

<400> SEQUENCE: 18
gtggcttgaa catttgtaat cttgcag                                              27

<210> SEQ ID NO 19
<211> LENGTH: 27
<212> TYPE: DNA
<213> ORGANISM: Artificial
<220> FEATURE:
<223> OTHER INFORMATION: V287I-R

<400> SEQUENCE: 19
aatgcttgaa catttgtaat cttgcag                                              27

<210> SEQ ID NO 20
<211> LENGTH: 27
<212> TYPE: DNA
<213> ORGANISM: Artificial
<220> FEATURE:
<223> OTHER INFORMATION: V287K-R

<400> SEQUENCE: 20
cttgcttgaa catttgtaat cttgcag                                              27

<210> SEQ ID NO 21
<211> LENGTH: 27
```

```
<212> TYPE: DNA
<213> ORGANISM: Artificial
<220> FEATURE:
<223> OTHER INFORMATION: V287L-R

<400> SEQUENCE: 21
gaggcttgaa catttgtaat cttgcag                                    27

<210> SEQ ID NO 22
<211> LENGTH: 27
<212> TYPE: DNA
<213> ORGANISM: Artificial
<220> FEATURE:
<223> OTHER INFORMATION: V287M-R

<400> SEQUENCE: 22
catgcttgaa catttgtaat cttgcag                                    27

<210> SEQ ID NO 23
<211> LENGTH: 27
<212> TYPE: DNA
<213> ORGANISM: Artificial
<220> FEATURE:
<223> OTHER INFORMATION: V287N-R

<400> SEQUENCE: 23
attgcttgaa catttgtaat cttgcag                                    27

<210> SEQ ID NO 24
<211> LENGTH: 27
<212> TYPE: DNA
<213> ORGANISM: Artificial
<220> FEATURE:
<223> OTHER INFORMATION: V287P-R

<400> SEQUENCE: 24
agggcttgaa catttgtaat cttgcag                                    27

<210> SEQ ID NO 25
<211> LENGTH: 27
<212> TYPE: DNA
<213> ORGANISM: Artificial
<220> FEATURE:
<223> OTHER INFORMATION: V287Q-R

<400> SEQUENCE: 25
ctggcttgaa catttgtaat cttgcag                                    27

<210> SEQ ID NO 26
<211> LENGTH: 27
<212> TYPE: DNA
<213> ORGANISM: Artificial
<220> FEATURE:
<223> OTHER INFORMATION: V287R-R

<400> SEQUENCE: 26
acggcttgaa catttgtaat cttgcag                                    27

<210> SEQ ID NO 27
<211> LENGTH: 27
<212> TYPE: DNA
<213> ORGANISM: Artificial
<220> FEATURE:
<223> OTHER INFORMATION: V287S-R

<400> SEQUENCE: 27
ggagcttgaa catttgtaat cttgcag                                    27
```

-continued

<210> SEQ ID NO 28
<211> LENGTH: 27
<212> TYPE: DNA
<213> ORGANISM: Artificial
<220> FEATURE:
<223> OTHER INFORMATION: V287T-R

<400> SEQUENCE: 28
ggtgcttgaa catttgtaat cttgcag                                            27

<210> SEQ ID NO 29
<211> LENGTH: 27
<212> TYPE: DNA
<213> ORGANISM: Artificial
<220> FEATURE:
<223> OTHER INFORMATION: V287W-R

<400> SEQUENCE: 29
ccagcttgaa catttgtaat cttgcag                                            27

<210> SEQ ID NO 30
<211> LENGTH: 27
<212> TYPE: DNA
<213> ORGANISM: Artificial
<220> FEATURE:
<223> OTHER INFORMATION: V287Y-R

<400> SEQUENCE: 30
atagcttgaa catttgtaat cttgcag                                            27

<210> SEQ ID NO 31
<211> LENGTH: 636
<212> TYPE: PRT
<213> ORGANISM: Luciola lateralis

<400> SEQUENCE: 31

Met Glu Asn Met Glu Asn Asp Glu Asn Ile Val Tyr Gly Pro Glu Pro
1               5                   10                  15

Phe Tyr Pro Ile Glu Glu Gly Ser Ala Gly Ala Gln Leu Arg Lys Tyr
            20                  25                  30

Met Asp Arg Tyr Ala Lys Leu Gly Ala Ile Ala Phe Thr Asn Ala Leu
        35                  40                  45

Thr Gly Val Asp Tyr Thr Tyr Ala Glu Tyr Leu Glu Lys Ser Cys Cys
    50                  55                  60

Leu Gly Glu Ala Leu Lys Asn Tyr Gly Leu Val Val Asp Gly Arg Ile
65                  70                  75                  80

Ala Leu Cys Ser Glu Asn Cys Glu Glu Phe Phe Ile Pro Val Leu Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Ala Ile Lys Thr Ile Val Ile Leu Asp Ser Lys Val Asp Tyr
145                 150                 155                 160

Arg Gly Tyr Gln Ser Met Asp Asn Phe Ile Lys Lys Asn Thr Pro Gln
                165                 170                 175

Gly Phe Lys Gly Ser Ser Phe Lys Thr Val Glu Val Asn Arg Lys Glu
            180                 185                 190

-continued

```
Gln Val Ala Leu Ile Met Asn Ser Ser Gly Ser Thr Gly Leu Pro Lys
            195                 200                 205
Gly Val Gln Leu Thr His Glu Asn Leu Val Thr Arg Phe Ser His Ala
            210                 215                 220
Arg Asp Pro Ile Tyr Gly Asn Gln Val Ser Pro Gly Thr Ala Ile Leu
225                 230                 235                 240
Thr Val Val Pro Phe His His Gly Phe Gly Met Phe Thr Thr Leu Gly
            245                 250                 255
Tyr Leu Thr Cys Gly Phe Arg Ile Val Met Leu Thr Lys Phe Asp Glu
            260                 265                 270
Glu Thr Phe Leu Lys Thr Leu Gln Asp Tyr Lys Cys Ser Ser Val Ile
            275                 280                 285
Leu Val Pro Thr Leu Phe Ala Ile Leu Asn Arg Ser Glu Leu Leu Asp
            290                 295                 300
Lys Tyr Asp Leu Ser Asn Leu Val Glu Ile Ala Ser Gly Gly Ala Pro
305                 310                 315                 320
Leu Ser Lys Glu Ile Gly Glu Ala Val Ala Arg Arg Phe Asn Leu Pro
            325                 330                 335
Gly Val Arg Gln Gly Tyr Gly Leu Thr Glu Thr Thr Ser Ala Ile Ile
            340                 345                 350
Ile Thr Pro Glu Gly Asp Asp Lys Pro Gly Ala Ser Gly Lys Val Val
            355                 360                 365
Pro Leu Phe Lys Ala Lys Val Ile Asp Leu Asp Thr Lys Lys Thr Leu
            370                 375                 380
Gly Pro Asn Arg Arg Gly Glu Val Cys Val Lys Gly Pro Met Leu Met
385                 390                 395                 400
Lys Gly Tyr Val Asp Asn Pro Glu Ala Thr Arg Glu Ile Ile Asp Glu
            405                 410                 415
Glu Gly Trp Leu His Thr Gly Asp Ile Gly Tyr Tyr Asp Glu Glu Lys
            420                 425                 430
His Phe Phe Ile Val Asp Arg Leu Lys Ser Leu Ile Lys Tyr Lys Gly
            435                 440                 445
Tyr Gln Val Pro Pro Ala Glu Leu Glu Ser Val Leu Leu Gln His Pro
            450                 455                 460
Asn Ile Phe Asp Ala Gly Val Ala Gly Val Pro Asp Pro Ile Ala Gly
465                 470                 475                 480
Glu Leu Pro Gly Ala Val Val Val Leu Glu Lys Gly Lys Ser Met Thr
            485                 490                 495
Glu Lys Glu Val Met Asp Tyr Val Ala Ser Gln Val Ser Asn Ala Lys
            500                 505                 510
Arg Leu Arg Gly Gly Val Arg Phe Val Asp Glu Val Pro Lys Gly Leu
            515                 520                 525
Thr Gly Lys Ile Asp Gly Lys Ala Ile Arg Glu Ile Leu Lys Lys Pro
            530                 535                 540
Val Ala Lys Gly Ser Met Glu Ala Pro Ala Ala Glu Ile Ser Gly
545                 550                 555                 560
His Ile Val Arg Ser Pro Met Val Gly Thr Phe Tyr Arg Thr Pro Ser
            565                 570                 575
Pro Asp Ala Lys Ala Phe Ile Glu Val Gly Gln Lys Val Asn Val Gly
            580                 585                 590
Asp Thr Leu Cys Ile Val Glu Ala Met Lys Met Met Asn Gln Ile Glu
            595                 600                 605
Ala Asp Lys Ser Gly Thr Val Lys Ala Ile Leu Val Glu Ser Gly Gln
```

-continued

```
            610                 615                 620
Pro Val Glu Phe Asp Glu Pro Leu Val Val Ile Glu
625                 630                 635
```

MUTANT FIREFLY LUCIFERASE, ITS GENE AND METHOD FOR PRODUCING MUTANT FIREFLY LUCIFERASE

CROSS-REFERENCE TO RELATED APPLICATION

This application is a United States national phase application of International Application PCT/JP2010/052253 filed Feb. 16, 2010.

BACKGROUND OF THE INVENTION

The present invention is an invention relating to the results of sponsored research for "Development of Systems and Technology For Advanced Measurement and Analysis, by the Japan Science and Technology Agency, 2008 and 2009".

TECHNICAL FIELD

The present invention relates to mutated firefly luciferase, a mutated firefly luciferase gene, novel recombinant DNA and a method for producing mutated firefly luciferase, and specifically, it relates to firefly luciferase with increased stability, its gene, and a method for producing stable firefly luciferase.

BACKGROUND ART

Firefly luciferase is an enzyme that, in the presence of magnesium ion and oxygen, converts adenosine triphosphate (ATP), D-luciferin and oxygen to adenosine monophosphate (AMP), oxyluciferin and carbon dioxide, generating light. Applying the light-generating principle of firefly luciferase allows very highly sensitive measurement of trace amounts of enzyme reaction substrate. Therefore, firefly luciferase is widely used, for example, for detection of microorganisms in food and beverage materials using ATP as the indicator, assessment of food residue or contamination adhering to fingers and implements, or high-sensitivity measurement using various antibody techniques or gene amplification techniques.

However, coleopteran luciferases such as firefly luciferase are generally unstable against heat, and therefore have the disadvantage of being easily inactivated when stored as reagents. In addition, coleopteran luciferases usually exhibit a drastically reduced luminescence amount once the luminescence amount has reached peak immediately after reaction, and therefore high-sensitivity measurement by prolonged reaction has been difficult to achieve. Therefore, efforts continue to be made to overcome these problems to obtain luciferase having satisfactory persistent luminescence or stability (thermostability and storage stability), and more preferably both.

One of these efforts is modification of the composition by addition of a salt or the like to the measuring reagent, to ensure some degree of persistent luminescence or storage stability. However, this method cannot be applied for a very wide range of different purposes and reagents due to constraints of the reagent composition, and in most cases, addition of the salt tends to elicit some sort of interference of the luciferase reaction.

A more preferred approach, one that has been attempted instead of modification of the reagent composition, is to search for mutant luciferases with preferred properties. As a result of such attempts, North American firefly luciferase has been obtained having the 342nd amino acid mutated to alanine, and it has been reported that the persistent luminescence of this firefly luciferase is increased (see Non-patent document 1, for example). In addition, the present applicant has obtained a Heike firefly (*Luciola lateralis*) variant corresponding to the aforementioned 342nd amino acid variant, i.e. Heike firefly luciferase having a mutation of the 344th amino acid (leucine) to alanine (hereunder referred to as "344A luciferase"), and has confirmed the same increase in persistent luminescence in this mutant firefly luciferase. However, the stability of this mutant firefly luciferase is extremely low compared to before introduction of the mutation. Thus, while 344A luciferase is imparted with the industrially useful property of persistent luminescence, its extremely low stability makes it difficult for it to be satisfactorily applied directly in high sensitivity assays and the like.

Thus, in the search for mutant luciferases having preferred properties, it commonly occurs that when a mutation is found that improves one property, the same mutation impairs a different property. That is, when several mutations which are each considered to be useful are introduced, the preferred properties of each are not obtained additively or synergistically, and this situation makes it even more difficult to obtain mutant luciferase exhibiting, in practice, multiple preferred properties such as persistent luminescence and stability.

[Non-patent document 1] Biochemistry 2003, Vol. 42, p 10429-10436

SUMMARY OF INVENTION

Technical Problem

It is an object of the present invention to provide a firefly luciferase with excellent stability, by introduction of a mutation at a specific nucleotide in the firefly luciferase gene sequence. It is another object of the invention to provide a firefly luciferase that, even when combined with a different mutation that contributes to persistent luminescence or the like, exhibits both of the preferred properties of stability and persistent luminescence without impairing either. It is yet another object of the invention to provide a firefly luciferase which, by addition of an additional mutation, has adequate recovery from reduction in stability caused by a mutation that gives a specific preferred effect but lowers the stability of firefly luciferase.

Solution to Problem

As a result of much diligent research directed toward solving the problems mentioned above, the present inventors have found that firefly luciferase stability is notably increased by a mutation of the amino acid of position 287 of Heike firefly or Japanese firefly (*Luciola cruciata*) luciferase to alanine (hereunder referred to as "287A mutation"), and by a mutation of the amino acid of position 392 to isoleucine (hereunder referred to as "392I mutation"). In addition, it was found that when either or both mutations, the 287A mutation and/or 392I mutation, are transferred in combination to 344A luciferase, the low stability that has been problematic with 344A luciferase is notably increased, and that the stability-increasing effect is satisfactorily exhibited even with further combined transfer of these mutations with other mutations. In addition, as a different mutation that increases the low stability of 344A luciferase, it was found that combined transfer of a mutation of the amino acid of position 326 to serine (hereunder referred to as "326S mutation") and a mutation of the amino acid of position 467 to isoleucine (hereunder referred to as "467I mutation") is effective, and the invention has thus been completed. Specifically, the invention relates to the following.

(1) Firefly luciferase having the amino acid sequence wherein the amino acid corresponding to position 287 of Heike firefly luciferase has been mutated to alanine, or wherein the amino acid corresponding to position 392 has been mutated to isoleucine.

(2) Firefly luciferase having the amino acid sequence wherein the amino acid corresponding to position 287 of Heike firefly luciferase has been mutated to alanine and the amino acid corresponding to position 392 has been mutated to isoleucine.

(3) Firefly luciferase according to (1) or (2) above, which has at least one mutation selected from among mutations wherein the amino acid corresponding to position 344 of Heike firefly luciferase has been mutated to alanine, the amino acid corresponding to position 326 has been mutated to serine, or the amino acid corresponding to position 467 has been mutated to isoleucine.

(4) Firefly luciferase according to (1) or (2) above, wherein the amino acid corresponding to position 344 of Heike firefly luciferase has been mutated to alanine, the amino acid corresponding to position 326 has been mutated to serine, and the amino acid corresponding to position 467 has been mutated to isoleucine.

(5) Firefly luciferase having a mutation in Heike firefly or Japanese firefly luciferase, wherein the amino acid of position 344 of the luciferase has been mutated to alanine, the amino acid of position 326 has been mutated to serine, and the amino acid of position 467 has been mutated to isoleucine.

(6) A firefly luciferase gene coding for firefly luciferase according to any one of (1) to (5) above.

(7) Recombinant DNA having a firefly luciferase gene according to (6) above inserted into vector DNA.

(8) A method for producing firefly luciferase with increased stability, characterized by culturing a microorganism comprising a firefly luciferase gene according to (6) above or recombinant DNA according to (7) above and being capable of producing firefly luciferase, and recovering firefly luciferase from the culture.

DESCRIPTION OF EMBODIMENTS

Figure 1:
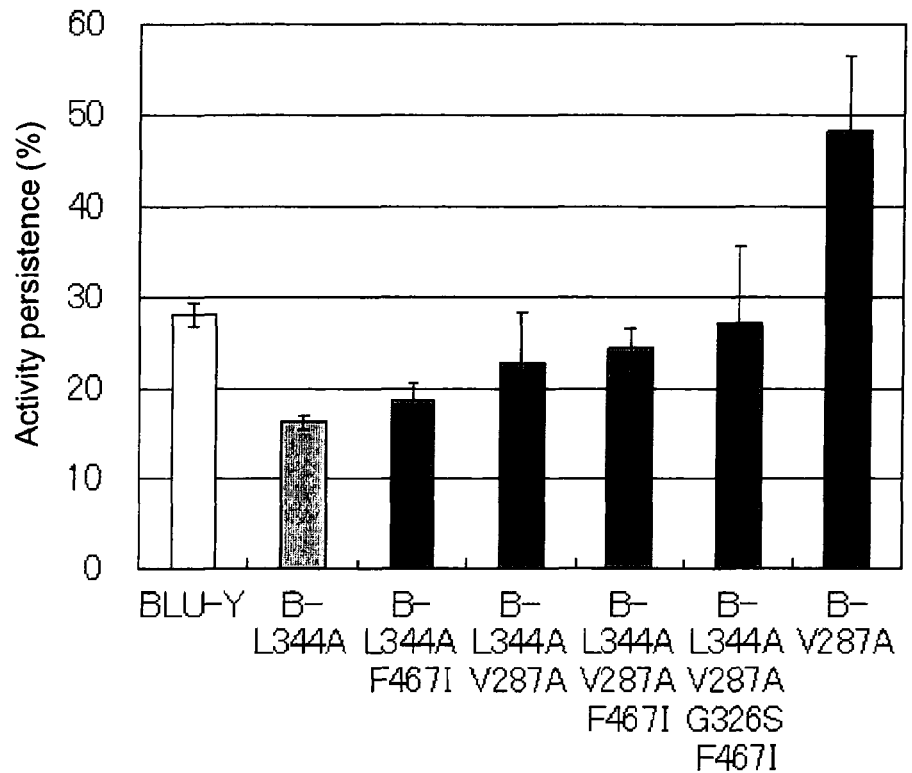
FIG. 1 is a graph showing the activity persistence after heat treatment of different firefly luciferases at 47° C. for 90 minutes.

The invention will now be explained in detail.
(Firefly Luciferase Gene and its Recombinant DNA)

The firefly luciferase gene of the invention and its recombinant DNA may by any one derived from firefly. For example, firefly luciferase derived from Heike firefly, Japanese firefly or North American firefly (*Photinus pyralis*) may be used. Alternatively, there may be used a chimeric gene prepared based on luciferase genes derived from different firefly species.

The firefly luciferase gene of the invention may also include mutations other than the mutations of the invention. Such mutations may be artificially introduced with the purpose of obtaining some specific effect, or they may be randomly or non-artificially introduced. Examples of mutations introduced with the purpose of obtaining specific effects include addition or modification of the sequence to augment the firefly luciferase gene expression level, modification to increase the firefly luciferase protein purification efficiency, and various mutations that impart practical desirable properties to firefly luciferase. Examples of such publicly known mutations include mutations that increase persistent luminescence as described in Japanese Unexamined Patent Application Publication No. 2000-197484, mutations that alter the luminous wavelength as described in Japanese Patent Publication No. 2666561 or Japanese Patent Public Inspection No. 2003-512071, mutations that increase surfactant resistance as described in Japanese Unexamined Patent Application Publication HEI No. 11-239493, mutations that increase substrate affinity as described in International Patent Publication No. WO99/02697, Japanese Patent Public Inspection HEI No. 10-512750 or Japanese Patent Public Inspection No. 2001-518799, and mutations that increase stability, as described in Japanese Patent Publication No. 3048466, Japanese Unexamined Patent Application Publication No. 2000-197487, Japanese Patent Public Inspection HEI No. 9-510610 and Japanese Patent Public Inspection No. 2003-518912.

These genes and recombinant DNA can be prepared according to known methods. For example, the Heike firefly luciferase gene and its recombinant DNA may be prepared by the method described in Japanese Examined Patent Application Publication HEI No. 7-112434, the Japanese firefly luciferase gene and its recombinant DNA may be prepared by the method described in Japanese Unexamined Patent Application Publication HEI No. 1-51086, or North American firefly luciferase gene and its recombinant DNA may be purchased from Promega Corp.
(Gene Mutations of the Invention and Corresponding Amino Acid Sequence Mutations)

The firefly luciferase gene of the invention has a specific mutation introduced into any of the aforementioned firefly luciferase genes. One mutant gene of the invention, in the case of Heike firefly or Japanese firefly, specifically, is a firefly luciferase gene coding for the 287A mutation amino acid sequence in which the amino acid of position 287 of luciferase (valine, for the wild type) is mutated to alanine. Another mutant gene of the invention, in the case of Heike firefly or Japanese firefly, specifically, is a firefly luciferase gene coding for the 392I mutation amino acid sequence in which the amino acid of position 392 of luciferase (valine, for the wild type) is mutated to isoleucine. Yet another mutant gene of the invention is the firefly luciferase gene coding for an amino acid sequence having at least one mutation selected from among 344A mutation in which the amino acid of position 344 of luciferase (leucine, for the wild type) has been mutated to alanine, 326S mutation in which the 326nd amino acid (glycine, for the wild type) has been mutated to serine, or 467I mutation in which the amino acid of position 467 (phenylalanine, for the wild type) has been mutated to isoleucine, in addition to the 287A mutation and/or 392I mutation mentioned above. Alternatively, it may be a firefly luciferase gene coding for the amino acid sequence of mutant luciferase having a combination of the 344A mutation, 326S mutation and 467I mutation.

The 287A mutation and/or 392I mutation in the amino acid sequence of Heike firefly luciferase or Japanese firefly luciferase notably increases the stability of firefly luciferase. The 326S mutation and 467I mutation also increase the stability of firefly luciferase. The amino acid sequence of the firefly luciferase of the invention preferably has a substitution for at least one of the aforementioned positions in the amino acid sequence of firefly luciferase, and more preferably it has a substitution at 2 or more positions and even more preferably 3 or more positions. By introducing these multiple mutations, it is possible to increase the stability of firefly luciferase in a stepwise manner. Specifically, by combining one or more mutations selected from among the 326S mutation and 467I mutation in addition to the 287A mutation and/or 392I mutation, the degree of improvement in the stability of firefly luciferase is increased. By introduction of these mutations, it is possible to effectively recover reduced stability when in combination with a different mutation that lowers the stability of firefly luciferase, such as the 344A mutation. In particular, introducing a combination of the 326S mutation and 467I mutation to firefly luciferase having the 344A mutation recovers the reduced stability of firefly luciferase. In other words, the mutations of the invention exhibit effects of increased stability of firefly luciferase compared to before mutation transfer, and of excellent recovery of stability even when combined with different mutations that significantly lower firefly luciferase stability.

Incidentally, "stability", for the purpose of the invention means thermostability and/or storage stability. Thermostability can be evaluated, for example, based on the residual activity after exposure of firefly luciferase to heat treatment at a prescribed temperature for a prescribed period of time.

Specifically, the thermostability of the firefly luciferase of the invention can be evaluated by comparing the activity persistence after heat treatment of firefly luciferase under high-temperature conditions, such as a reaction temperature of usually 40-60° C. and preferably 45-55° C., for a prescribed period of time such as generally 10-180 minutes, or 60-180 minutes, for example. The activity persistence of the firefly luciferase of the invention is calculated as the ratio of firefly luciferase activity after heat treatment with respect to the activity before use under the aforementioned high-temperature conditions. Increase in thermostability according to the invention means that the activity persistence, after firefly luciferase has been used under the conditions specified above, increases at least 1.2-fold with respect to absence of a mutation of the invention.

The storage stability of firefly luciferase according to the invention can be evaluated based on the residual activity when firefly luciferase has been stored for a prescribed period of time at a prescribed temperature. Increase in storage stability according to the invention means that the activity persistence, after firefly luciferase has been used under the conditions specified above, is more than equivalent with respect to absence of a mutation of the invention.

Such a degree of increase in thermostability and/or storage stability according to the invention is difficult to easily achieve, and is notable among attempts to introduce mutations for increased stability of firefly luciferase, and it therefore constitutes a useful improvement for practical use of firefly luciferase.

(Numbers for Firefly Luciferase Gene Sequence and Amino Acid Sequence)

The numbers indicating the positions of mutations in the gene sequences and amino acid sequences of firefly luciferase, according to the invention, are based on the numbers for wild type Heike firefly luciferase or Japanese firefly luciferase. Specifically, when the invention is to be applied to a luciferase other than wild type Heike firefly luciferase, the mutation positions in the gene sequence and amino acid sequence are the corresponding positions in each firefly luciferase, when replaced at the equivalent positions in wild type Heike firefly luciferase or Japanese firefly luciferase. As specific examples, the positions of the amino acids equivalent to the 287th, 326th, 392nd and 467th positions of Heike firefly luciferase or Japanese firefly luciferase are, respectively, the positions 285, 324, 390 and 465 in North American firefly luciferase.

This corresponding relationship can be easily established by comparison between the amino acid sequence of each luciferase and the amino acid sequence of Heike firefly luciferase using, for example, amino acid homology analysis software such as GENETYX-Mac (product of Software Development). In actuality, commonalities are seen in the amino acid sequences of Heike firefly luciferase, Japanese firefly luciferase and North American firefly luciferase, as well as structural similarities based thereon, and introduction of the same mutations at corresponding positions are known to exhibit similar effects on the properties of the firefly luciferases. Consequently, utilizing the knowledge of the mutations of the invention exhibited in Heike firefly luciferase, it is possible to easily attempt introduction of the same mutations at corresponding positions in Japanese firefly luciferase or North American firefly luciferase, with the aim of obtaining the same effect.

(Introduction of Mutations)

The mutated firefly luciferase gene can be satisfactorily obtained by modifying the firefly luciferase gene by any known method. Widely used gene modification methods include methods of introducing site-specific mutations, methods of introducing random mutations, methods using mutagenic agents, ultraviolet irradiation methods, and protein engineering methods.

Examples of mutagenic agents to be used for mutation include hydroxylamine, N-methyl-N'-nitrosoguanidine (NTG), nitrous acid, sulfurous acid, hydrazine, formic acid and 5-bromouracil. The agent treatment is not particularly restricted so long as it can induce the desired mutations in the firefly luciferase gene, and the optimal conditions for the type of agent used may be employed. For example, desired mutations can be induced by treatment with a 0.5-12 M agent concentration at 20-80° C. for 10 minutes or longer, and specifically, 10-180 minutes.

Ultraviolet irradiation may be carried out by a known method, such as the method described in Gendai Kagaku pp 24-30, June, 1989.

A common method that takes advantage of protein engineering is site-specific mutagenesis. Examples of the method are the Kramer method (Kramer, W. et al., Nucleic Acids Res, vol. 12, pp 9441-9456 (1984): Kramer, W. et al., Methods Enzymol, vol. 154, pp 350-367 (1987): Bauer, C. E. et al., Gene, vol. 37, pp 73-81 (1985)), the Eckstein method (Taylor, J. W. et al., Nucleic Acids Res, vol. 13, pp 8749-8764 (1985): Taylor, J. W. et al., Nucleic Acids Res, vol. 13. pp 8765-8785 (1985): Nakamaye, K. L. et al., Nucleic Acids Res, vol. 14, pp 9679-9698 (1986)), and the Kunkel method (Kunkel, T. A., Proc. Natl. Acids Sci. U.S.A., vol. 82, pp 488-492 (1985): Kunkel, T. A. et al., Methods Enzymol, vol. 154, pp 367-382 (1987).

There may also be used the method commonly known as the Polymerase Chain Reaction [Technique, 1, 11 (1989)].

In addition to gene modification methods, a desired modified firefly luciferase gene can also, of course, be directly synthesized by organic synthesis methods or enzyme synthesis methods. Determination and confirmation of the nucleotide sequence of the desired firefly luciferase gene obtained by such a method can be accomplished by the Maxam-Gilbert chemical modification method [Maxam-Gilbert, Meth. Enzym., vol. 65, pp 499-560 (1980)] or the dideoxynucleotide chain termination method using M13 phage [Messing et al., Gene, vol. 19, pp 269-276 (1982)].

(Preparation of Vectors and Transformants)

The mutant firefly luciferase gene obtained as described above may be incorporated by a common method into a vector such as a bacteriophage, cosmid, or a plasmid used for transformation of prokaryotic cells or eukaryotic cells, and the vector used by a common method for transformation or transfection of a host.

Any host may be used, but microbes, for example, are preferred. Specifically, a microorganism belonging to the genus *Escherichia* may be used. Examples of microorganisms belonging to the genus *Escherichia* include *E. coli* K-12, JM109, DH5α, HB101 and BL21.

Moreover, by screening for strains that are able to produce firefly luciferase with the desired mutation, from among the resulting transformed or transfected host cells, it is possible to obtain strains that can produce mutated firefly luciferase. To obtain novel recombinant DNA purified from a strain obtained in this manner there may be used, for example, the method of Guerry [J. Bacteriology, 116, 1604 (1973)] or the method of Clewell [J. Bacteriology, 110, 667 (1972)].

To obtain DNA comprising the mutated firefly luciferase gene from obtained recombinant DNA, there may be used a known method, such as a method of reacting a restriction enzyme with the plasmid DNA for 1-24 hours at a reaction temperature of 30-40° C., and subjecting the reacted solution to agarose gel electrophoresis (see Molecular Cloning, 150, Cold Spring Harbor Laboratory (1982)).

(Production of Mutant Firefly Luciferase)

For production of mutated firefly luciferase of the invention using a strain capable of producing the mutant firefly luciferase, obtained as described above, the strain capable of producing the mutant firefly luciferase may be cultured by any of various known methods. Culturing may be accomplished by a common solid culturing method, but if possible it is preferably accomplished by a liquid culturing method.

The medium used for culturing of the strain may be, for example, one obtained by adding one or more inorganic salts such as sodium chloride, monopotassium phosphate, dipotassium phosphate, magnesium sulfate, magnesium chloride, ferric chloride, ferric sulfate or manganese sulfate, to one or more nitrogen sources such as yeast extract, tryptone, peptone, meat extract, corn steep liquor or soybean or wheat bran exudate, and further adding appropriate amounts of sugar materials, vitamins and the like as necessary.

The initial pH of the medium is suitably adjusted to pH 7-9. The culturing is preferably carried out by submerged culture, shaking culture, stationary culture or the like, at 30-40° C. and preferably about 37° C., for 4-24 hours and preferably 6-8 hours. A common known enzyme harvesting method may be used to obtain the firefly luciferase with increased stability from the culture after completion of the culturing.

Specifically, the cells may be subjected to ultrasonic disruption treatment, grinding treatment or the like by a common method, or a bacteriolytic enzyme such as lysozyme may be used to extract the firefly luciferase with increased stability, or they may be shaken or stationed in the presence of an organic solvent such as toluene for autodigestion, and the firefly luciferase excreted out of the cells. The obtained extract or autodigestion product is supplied to filtration, centrifugal separation and the like to remove the solid components, and if necessary the nucleic acid is removed with streptomycin sulfate, protamine sulfate, manganese sulfate or the like, after which ammonium sulfate, alcohol or acetone is added and fractionation performed, to obtain a crude enzyme.

The crude enzyme may be subjected to known techniques, such as a gel filtration method using Sephadex, Ultrogel, Bio-Gel or the like; an adsorption-elution method using an ion exchanger; an electrophoresis method using polyacrylamide gel; an adsorption-elution method using hydroxyapatite; a precipitation method such as sucrose density gradient centrifugation; an affinity chromatography method, or a fractionation method using a molecular sieving membrane or hollow fiber membrane, appropriately selected in any desired combination, to obtain a highly-purified enzyme preparation.

The present invention will now be explained in greater detail by the following examples.

Example 1

Construction of Plasmid pET16b-BLU-Y

A full-length primer (SEQ ID NO: 1) was synthesized for amplification of a biotinylated luciferase structural gene. Using plasmid pHLf248 described in Japanese Patent No. 3466765 (*E. coli* JM101[pHLf248] including this plasmid has been deposited at the National Institute of Advanced Industrial Science and Technology, International Patent Organism Depositary (IPOD) as FERM BP-5081) as template, a DNA fragment was amplified by PCR using the aforementioned full-length primer and commercially available M13-M4 primer (product of Takara Bio, Inc.). The obtained DNA fragment was digested using NdeI and HindIII and then subjected to agarose gel electrophoresis, and a DNA fragment was purified from the 1.9 kb band.

Next, the DNA fragment was inserted into NdeI- and HindIII-digested plasmid vector pET16b (product of Novagen) by an established method, to construct plasmid pET16b-BLU-Y.

The constructed plasmid pET16b-BLU-Y was also transferred into *E. coli* JM109 for transformation. After purifying the plasmids from the obtained transformants, the DNA sequence was confirmed. The amino acid sequence of firefly luciferase (BLU-Y) deduced from the firefly luciferase gene in the DNA sequence was the same as listed in Japanese Patent No. 3466765.

Example 2

Construction of Plasmid Containing Mutant Firefly Luciferase Gene

The following procedure was carried out to construct a plasmid (pHLf344A) containing a gene coding for luciferase having the 344th amino acid residue leucine mutated to alanine (344A mutation) in the amino acid sequence of Heike firefly luciferase.

First, there were synthesized PCR primers designed to convert the 344th amino acid residue leucine to alanine ((pHLf344A F-344A (SEQ ID NO: 2), pHLf344A R-344A (SEQ ID NO: 3)). These primers were used for PCR amplification with pET16b-BLU-Y as template (according to established reaction protocols and conditions). The amplified PCR reaction mixture was digested with DpnI, and the PCR product ends were phosphorylated by kinase treatment. Next, a Ligation Convenience Kit (product of Nippon Gene Co., Ltd.) was used for self-ligation of the DpnI- and kinase-treated PCR reaction product, to obtain pHLf344A. Following the method of D. M. Morrison (Methods in Enzymology, 68, p. 326-331, 1979), pHLf344A was used for transformation of *E. coli* JM109, the plasmids were purified from the obtained JM109 transformants, and the sequence of the DNA coding for mutant luciferase in pHLf344A was confirmed (SEQ ID NO: 4). The amino acid sequence deduced from the DNA sequence had the 344th amino acid residue leucine of the amino acid sequence corresponding to the luciferase gene in pET16b-BLU-Y obtained in Example 1, converted to alanine.

Plasmids containing genes coding for luciferase artificially combining mutations discovered according to the invention, or luciferase having mutations discovered according to the invention replaced by different amino acids, were constructed by the procedure described above.

Example 3

Obtaining Mutant Firefly Luciferase with Increased Stability

The recombinant plasmid pHLf344A of Example 2 was used as template for error-prone PCR using primers designed upstream and downstream from the mutant luciferase gene region (SEQ ID NO: 5 and 6). Specifically, the primers were used at a final concentration of 0.2 µM, and Ex-Taq (product of Takara Bio, Inc.) was used with a manganese ion concentration of 0.1 mM and a magnesium ion concentration of 6.5 mM, for PCR amplification reaction of the pHLf344A gene region, to obtain firefly luciferase gene fragments having different mutations introduced therein. After then performing restriction enzyme treatment with NdeI and HindIII, the fragments were separated by agarose gel electrophoresis and a RECO-CHIP (product of Takara Bio, Inc.) was used to recover the DNA fragments from the electrophoresed gel. The obtained DNA fragments were ligated to pHLf344A vector obtained by NdeI and HindIII treatment of pHLf344A, using a Ligation Convenience Kit (product of Nippon Gene Co., Ltd.). Upon completion of the ligation, the mutation-transferred recombinant plasmid DNA was used for transformation of *E. coli* BL21 (DE3) (product of Invitrogen Corp.), according to the method described above, to create a mutant library. The transformants were inoculated in LB-amp agar medium [bactotryptone: 1% (w/v), yeast extract: 0.5% (w/v), NaCl: 10.5% (w/v), ampicillin: (50 µg/ml) and agar: 1.4% (w/v)], and plate culture was carried out at 37° C.

After 12 hours, each of the appeared colonies were inoculated in LB-IPTG-amp agar medium [1% (w/v) bactotryptone, 0.5% (w/v) yeast extract, 10.5% (w/v) NaCl, 1 mM isopropyl-β-D-thiogalactopyranoside, 50 µg/ml ampicillin and 1.4% (w/v) agar], and plate culture was carried out at 30° C. After culturing for 12-18 hours, the cells were covered with a nitrocellulose filter (product of Advantech, Inc.) and the colonies were transferred into a filter and supplied for heat treatment at 55° C. for 30 minutes together with the filter, after which the heat-treated filter was dipped in a luminescent reagent [100 mM Na-citrate, 1 mM Luciferin, 10 mM $MgSO_4$, pH 5.0], and LAS-3000 (product of FujiFilm Corp.) was used to photograph the luminescence of the colonies under the following conditions (Method: Chemiluminescence, Exposure Type: Increment, Exposure Time: 10-30 sec).

The firefly luciferases in the strains confirmed to have luminescence even after heat treatment were selected as candidate mutants with increased stability.

Example 4

Confirmation of Mutation Positions

The strains selected in Example 3 were cultured in 2 ml of LB-IPTG-amp medium. After culturing for 18-24 hours, the cells were collected by centrifugal separation and then suspended in 50 mM potassium phosphate buffer, 0.2% (w/v) BSA (product of Wako Pure Chemical Industries, Ltd.) at pH 7.5 and subjected to ultrasonic disruption, to obtain a crude enzyme solution. A mixture of 1-10 µl of the crude enzyme solution added to 0.3 M Tricine-NaOH, 0.2% BSA, 5% Glycerol, at pH 7.8 was supplied to heat treatment for 90 minutes at a reaction temperature of 47° C. An activity measuring reagent [50 mM Tricine-NaOH, 4 mM ATP, 2 mM Luciferin, 10 mM $MgSO_4$, pH 7.8] was used to measure the luciferase crude enzyme activity before and after heat treatment. The luciferase activity was evaluated by the cumulative luminescence amount obtained in 1 second using a luminometer (LB96V by Berthold Co., Ltd.), and the ratio of the luminescence amount after heat treatment with respect to the luminescence amount before heat treatment was calculated as the "activity persistence". Candidate strains with greater activity persistence than the parent strain were designated as increased stability mutants, and a CEQ2000 DNA Sequencing System (Beckman Coulter, Inc.) was used to determine the sequences of the firefly luciferase genes coding in the plasmids in the increased stability mutants.

As a result, the gene sequences of 4 candidate strains were confirmed to code for mutated firefly luciferase comprising an amino acid sequence in which valine at position 287 is replaced with alanine (SEQ ID NO: 7), or an amino acid sequence in which glycine at position 326 is replaced with serine (SEQ ID NO: 8), or an amino acid sequence in which valine at position 392 is replaced with isoleucine (SEQ ID NO: 9), or an amino acid sequence in which phenylalanine at position 467 is replaced with isoleucine (SEQ ID NO: 10). The gene sequence coding for the amino acid sequence of firefly luciferase in which valine at position 287 is replaced with alanine is listed as SEQ ID NO: 11.

Also, information of the positions of the mutations in the obtained mutants was utilized by the methods described in the previous examples to construct new mutants having mutations which were a combination of the aforementioned mutations, or mutants with the mutations replaced with other amino acids, to obtain different mutant firefly luciferases.

Example 5

Evaluation of Mutant Firefly Luciferase Stability

The obtained mutant firefly luciferases having different amino acid sequences were subjected to heat treatment by the method described in Example 4, and then the luciferase activity was measured to evaluate the activity persistence after heat treatment (47° C., 90 minutes). The results are shown in FIG. 1.

1. Evaluation of 287A Mutation Firefly Luciferase Stability

The activity persistence after heat treatment was 28.1% with luciferase lacking a mutation of the invention (BLU-Y), but was significantly increased to 48.3% (1.7-fold) with luciferase having the 287A mutation (B-V287A). This indicated that the 287A mutation has a major effect of increasing the thermostability of luciferase.

The same 287A mutant was created for Japanese firefly luciferase as well, following the procedure in Examples 2 to 5, and the thermostability of the obtained 287A mutant was evaluated. The amino acid sequence of LcrL is as listed in Japanese Patent Publication No. 3048466, and it is a mutant with threonine at position 217 replaced with leucine.

As a result, the activity persistence of luciferase without the Japanese firefly luciferase 287A mutation (LcrL) after heat treatment was 10.1%, whereas the activity persistence of mutant luciferase with the 287A mutation (LcrL-V287A) after heat treatment was 14.7% (1.5-fold increase).

That is, it was confirmed that the 287A mutation increases the thermostability of not only Heike firefly luciferase but also Japanese firefly luciferase.

2. Evaluation of 392I Mutation Firefly Luciferase Stability

The activity persistence of mutant firefly luciferase with the 392I mutation after heat treatment was increased to 45.5%, which was a 1.5-fold increase over BLU-Y. This indicated that the 392I mutation is effective for increasing the thermostability of luciferase.

The same 392I mutant was created for Japanese firefly luciferase as well, following the procedure in Examples 2 to 5, and the thermostability of the obtained 392I mutant was evaluated. As a result, the activity persistence of luciferase without the Japanese firefly luciferase 392I mutation (LcrL) after heat treatment was 10.7%, whereas the activity persistence of mutant luciferase with the 392I mutation (LcrL-V392I) after heat treatment was 16.2% (1.5-fold increase).

That is, it was confirmed that the 392I mutation increases the thermostability of not only Heike firefly luciferase but also Japanese firefly luciferase.

3. Evaluation of Stability of Firefly Luciferase Containing 287A Mutation and 392I Mutation The activity persistence of mutant luciferase comprising a combination of the 287A mutation and 392I mutation was measured to be 58.5%, which was a 1.9-fold increase over BLU-Y. Specifically, it was confirmed that a combination of the two mutations increased the thermostability compared to mutant luciferase with only either the 287A mutation or 392I mutation.

That is, the combination of the 287A mutation and 392I mutation was shown to be even more effective for increasing thermostability.

4. Evaluation of Stability of Firefly Luciferases Containing Other Mutation Combinations The activity persistence with combination of the 344A mutation, which impairs luciferase thermostability, with BLU-Y (B-L344A) was reduced to 16.2%, but with additional combination of the 287A mutation (B-L344A V287A), the activity persistence was recovered to 22.7%, which was a 1.4-fold increase over B-L344A. With combination of the 467I mutation with the 344A mutation (B-L344A F467I) or combination of the 326S mutation with the 344A mutation (data not shown in the graph), the stability was increased over B-L344A, but not exceeding 1.2-fold, and therefore the increasing effect was not adequate compared to the effect with combination of the 287A mutation. However, when these mutations were each combined with the 287A mutation, the thermostability-increasing effect of the 287A mutation was either maintained or further increased, and for example, the activity persistence with B-L344A V287A F467I was recovered to 24.3%, which was a 1.5-fold increase over B-L344A.

A North American firefly luciferase mutant (F465R) having the mutation position of F467 has been reported in International Patent Publication No. WO2007/017684, but no recovery from the reduced stability by the L344A mutation was seen with combination of this mutation.

Also, in a strain having 3 different mutations introduced with 344A (B-L344A V287A G326S F467I, hereunder referred to as "triple mutant"), the activity persistence was increased to 27.3%, which was a 1.7-fold increase over L344A. Furthermore, with a quadruple mutant additionally having a 392I mutation in the triple mutant (B-L344A V287A G326S F467I V392I), the activity persistence was further increased, with a 1.6-fold increase being exhibited compared to BLU-Y which did not contain the 344A mutation (data not shown in the graph).

Even with a strain not having the 287A mutation but having a combination of the 467I mutation and 326S mutation with the 344A mutation (B-L344A G326S F467I), the activity persistence was increased to 21.5%, which was a 1.3-fold increase over B-L344A.

5. Evaluation of Stability of Mutants with the V287 Position Mutated to Different Amino Acids Plasmids were constructed coding for luciferase genes of a Heike firefly luciferase 344A mutant, having the valine at position 287 mutated to 18 different amino acids other than alanine. Transfer of the mutations by PCR was accomplished by the transfer method for the 344A mutation described in Example 2, and the primers used were SEQ ID NO: 12 to SEQ ID NO: 30. The same forward primer (Primer F (SEQ ID NO: 12)) was used for construction of all of the amino acid mutants in the PCR. The reverse primers used for PCR (V287C-R (SEQ ID NO: 13), V287D-R (SEQ ID NO: 14), V287E-R (SEQ ID NO: 15), V287F-R (SEQ ID NO: 16), V287G-R (SEQ ID NO: 17), V287H-R (SEQ ID NO: 18), V287I-R (SEQ ID NO: 19), V287K-R (SEQ ID NO: 20), V287L-R (SEQ ID NO: 21), V287M-R (SEQ ID NO: 22), V287N-R (SEQ ID NO: 23), V287P-R (SEQ ID NO: 24), V287Q-R (SEQ ID NO: 25), V287R-R (SEQ ID NO: 26), V287S-R (SEQ ID NO: 27), V287T-R (SEQ ID NO: 28), V287W-R (SEQ ID NO: 29), V287Y-R (SEQ ID NO: 30)) differed according to the type of amino acid.

In the mutants having the valine at position 287 of the 344A mutation mutated to the 18 different amino acids other than alanine (B-L344A V287X), differences were seen in the activity and stability depending on the type of amino acid at position V287. Almost all of the luciferase activity was lost in the mutants having the amino acids Asp, Glu, Phe, Gly, His, Lys, Asn, Pro, Gln, Arg, Trp and Tyr substituting at position 287. Of the 287 mutants retaining luciferase activity, the activity persistence after heat treatment in the mutants with substitution of Leu, Ile, Cys, Met, Ser and Thr was reduced to 0.25-0.8 times that of the 344A mutant. The results are shown in Table 1.

That is, the only 287-position mutant exhibiting sufficient luciferase activity and thermostability-increasing effect was the one wherein the amino acid at position 287 was replaced with alanine.

TABLE 1

| Mutant name | Activity persistence (%) | Relative activity persistence (%) |
| --- | --- | --- |
| B-344A | 13.1 | 1.00 |
| B-344A V287A | 16.8 | 1.28 |
| B-344A V287C | 9.8 | 0.75 |
| B-344A V287I | 10.5 | 0.80 |
| B-344A V287L | 9.3 | 0.71 |
| B-344A V287M | 10.1 | 0.77 |
| B-344A V287S | 3.4 | 0.26 |
| B-344A V287T | 4.9 | 0.37 |

6. Evaluation of Thermostability at Different Treatment Temperatures

Figure 2:
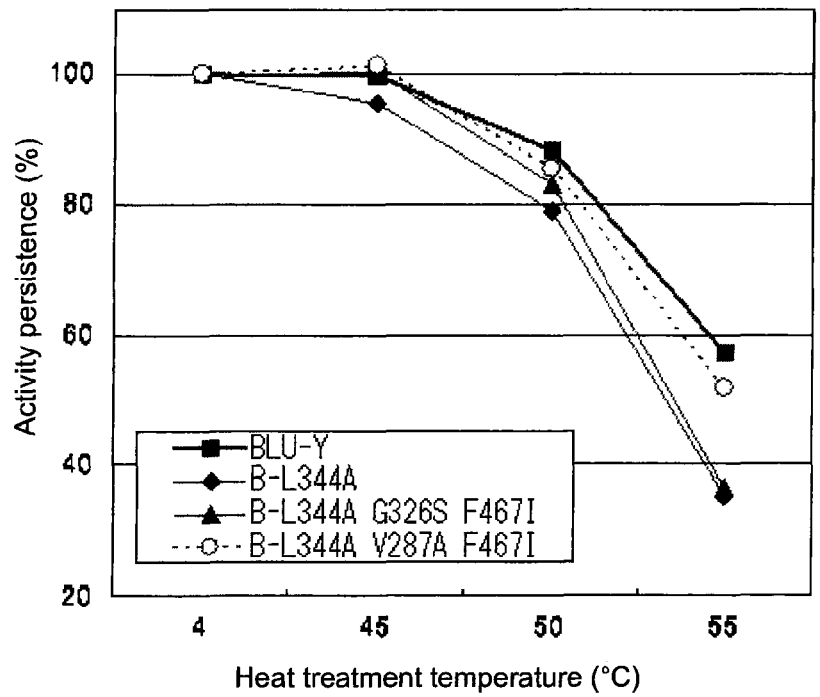
FIG. 2 is a graph showing the activity persistence after heat treatment of different firefly luciferases at 4° C., 45° C., 50° C. and 55° C. for 10 minutes.

FIG. 2 shows the data from evaluation of the activity persistence for different luciferases during 10 minutes at heat treatment temperatures of 4° C., 45° C., 50° C. and 55° C. It was confirmed that, for heat treatment at 45° C., 50° C. and 55° C., transfer of mutations of the invention improved the weakened thermostability by L344A mutation.

Example 6

Persistent Luminescence of Mutant Firefly Luciferase

A luminometer (LB96V by Berthold Co., Ltd.) was used to confirm the persistent luminescence of each mutant tested in Example 5 [Reaction reagents: 50 mM Tricine-NaOH, 0.8 mM ATP, 0.5 mM Luciferin, 10 mM $MgSO_4$, 0.2% BSA, 2% Sucrose, 1 mM EDTA]. The persistent luminescence was determined by obtaining measured values from 1.2 seconds to 60 seconds after start of the measurement, and calculating the ratio of the measured value after 60 seconds with respect to the measured value after 1.2 seconds (persistence of luminescence). That is, a low ratio of the measured value after 60 seconds with respect to the measured value after 1.2 seconds indicates large attenuation of luminescence, and poor persistent luminescence.

The results showed that in firefly luciferase without the L344A mutation (BLU-Y) the persistent luminescence was 27.8%, with attenuation to less than ⅓ the luminescence amount by 60 seconds, while the persistent luminescence was 100-150% with all of the mutant firefly luciferases containing the L344A mutation, as a persistent luminescence mutation. That is, it was demonstrated that all of the mutants containing stability mutations of the invention and having the L344A mutation maintained satisfactory persistent luminescence as the effect of L344A mutation, while exhibiting a thermostability-increasing effect.

Example 7

Mutant Firefly Luciferase Storage Stability

Figure 3:
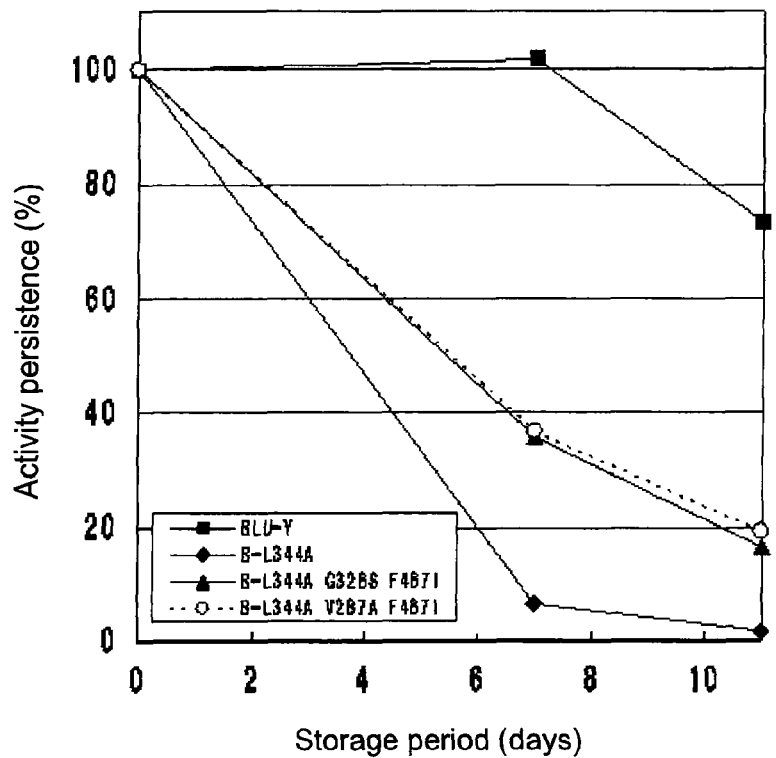
FIG. 3 is a graph showing the activity persistence after storage of different firefly luciferases at 37° C. for 11 days.
Figure 4:
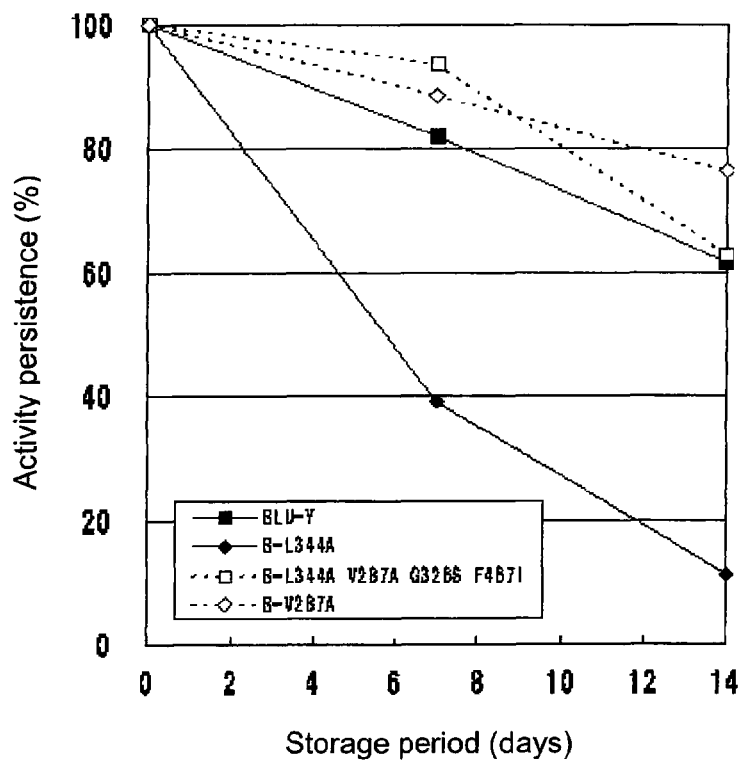
FIG. 4 is a graph showing the activity persistence after storage of different firefly luciferases at 37° C. for 14 days.

Each of the mutant firefly luciferases was stored at different temperatures and the activity persistence after storage was evaluated. Examples of data after storage for 11 days and 14 days at 37° C. at a concentration of 0.1 µg/mL are shown in FIG. 3 and FIG. 4 (Storage solution composition: 0.1 M potassium phosphate buffer (pH 7.0), 2 mM EDTA 2Na, 0.2% BSA (product of Wako Pure Chemical Industries, Ltd.), 0.02% casein, 0.05% $NaN_3$). Both tests were carried out separately, with the activity at the start of the storage test being defined as 100%.

In both FIG. 3 and FIG. 4, the activity persistence after storage was drastically reduced with the L344A mutation firefly luciferase compared to firefly luciferase without the L344A mutation (BLU-Y). In contrast, all of the mutant firefly luciferases having mutations of the invention introduced in combination with the L344A mutation had improvement in the reduced activity persistence after storage. For example, with the mutant firefly luciferase having a combination of the 3 mutations L344A G326S F467I (activity persistence: 16%) and the mutant firefly luciferase having a combination of the 3 mutations L344A V287A F467I, the activity persistence after storage was increased compared to L344A (activity persistence: 2%). In addition, with the mutant firefly luciferase having a combination of the 4 mutations L344A V287A G326S F467I and the firefly luciferase having the V287A mutation introduced into BLU-Y, the activity persistence after storage was significantly increased, and satisfactory storage stability superior to BLU-Y was exhibited.

As these results demonstrate, the method of the invention allows firefly luciferase with excellent stability to be efficiently produced and provided. Moreover, it is possible to efficiently produce and provide firefly luciferase exhibiting both the property of persistent luminescence, and stability. According to the invention there is provided firefly luciferase with excellent stability, which can be advantageously utilized for high-sensitivity measurement of luminescence and in kits for microassay of ATP and the like, while combination with other useful mutations such as persistent luminescence mutations is expected to allow its application in an even wider range of uses.

SEQUENCE LISTING

The invention claimed is:

1. An isolated luciferase polypeptide consisting of the amino acid sequence of SEQ ID NO: 31, and wherein the valine at position 287 of SEQ ID NO: 31 is replaced with alanine.

2. An isolated polynucleotide encoding the luciferase polypeptide according to claim 1.

3. A recombinant vector comprising the isolated polynucleotide according to claim 2.

4. A method for producing a luciferase polypeptide comprising culturing a microorganism transformed with the isolated polynucleotide according to claim 2 to produce the luciferase polypeptide, and recovering the luciferase polypeptide from the culture.

* * * * *